(12) United States Patent
Hart et al.

(10) Patent No.: US 11,810,040 B2
(45) Date of Patent: *Nov. 7, 2023

(54) METHOD AND SYSTEM FOR MONITORING CORE BODY MOVEMENTS

(71) Applicant: SOTER ANALYTICS PTY LTD, Como (AU)

(72) Inventors: Matthew Hart, Como (AU); Alexey Pavlenko, Como (AU)

(73) Assignee: SOTER ANALYTICS PTY LTD, Como (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/519,274

(22) Filed: Nov. 4, 2021

(65) Prior Publication Data

US 2022/0058537 A1 Feb. 24, 2022

Related U.S. Application Data

(63) Continuation of application No. 16/622,671, filed as application No. PCT/AU2018/050600 on Jun. 18, 2018, now Pat. No. 11,182,723.

(30) Foreign Application Priority Data

Jun. 16, 2017 (AU) ................................ 2017902302

(51) Int. Cl.
*G06Q 10/0635* (2023.01)
*G16H 20/30* (2018.01)
(Continued)

(52) U.S. Cl.
CPC ........ *G06Q 10/0635* (2013.01); *A61B 5/1116* (2013.01); *A61B 5/7275* (2013.01); *A61B 5/742* (2013.01); *G01P 3/00* (2013.01); *G16H 20/30* (2018.01); *G16H 50/30* (2018.01); *A61B 2503/20* (2013.01)

(58) Field of Classification Search
CPC .... G06Q 10/0635; G16H 20/30; G16H 50/30; A61B 5/1116; A61B 5/7275; A61B 5/742; A61B 2503/20; G01P 13/00
See application file for complete search history.

(56) References Cited

U.S. PATENT DOCUMENTS 7,335,167 B1 2/2008 Mummy
8,328,691 B2 12/2012 Lanfermann et al.
(Continued)

FOREIGN PATENT DOCUMENTS

WO 2015/172096 A1 11/2015
WO 2016/126639 A1 8/2016

OTHER PUBLICATIONS

Sep. 17, 2019—(WO) IPRP—App PCT/AU2018/050600.
Sep. 17, 2018—(WO) Search Report and Written Opinion—App PCT/AU2018/050600.

*Primary Examiner* — Mohamed Barakat
*Assistant Examiner* — Rufus C Point
(74) *Attorney, Agent, or Firm* — Banner & Witcoff, Ltd.

(57) ABSTRACT

A system for monitoring core body movement comprises a sensor device for collecting a data set representing a plurality of core body movements over time from a monitoring device; a processor for determining a plurality of risk scores from the data set; and an output device for indicating the risk scores.

14 Claims, 9 Drawing Sheets

(51) Int. Cl.
    *G16H 50/30* (2018.01)
    *A61B 5/11* (2006.01)
    *A61B 5/00* (2006.01)
    *G01P 13/00* (2006.01)
    *G01P 3/00* (2006.01)

(56) References Cited

U.S. PATENT DOCUMENTS

| | | |
|---|---|---|
| 8,918,883 B1 | 12/2014 | Boyle et al. |
| 9,149,195 B2 * | 10/2015 | Hadley ............... G16H 50/30 |
| 9,223,936 B2 | 12/2015 | Aragones et al. |
| 10,631,732 B2 | 4/2020 | Larson et al. |
| 2003/0226695 A1 | 12/2003 | Mault |
| 2005/0027216 A1 | 2/2005 | Guillemaud et al. |
| 2007/0219059 A1 | 9/2007 | Schwartz et al. |
| 2009/0076410 A1 | 3/2009 | Libbus et al. |
| 2009/0135009 A1 * | 5/2009 | Little ............... G06Q 40/08 705/4 |
| 2011/0082350 A1 | 4/2011 | Koh |
| 2012/0065524 A1 | 3/2012 | Morren et al. |
| 2012/0253484 A1 | 10/2012 | Burich et al. |
| 2012/0254934 A1 | 10/2012 | McBrearty et al. |
| 2012/0259652 A1 | 10/2012 | Mallon et al. |
| 2014/0081179 A1 | 3/2014 | Moore-Ede |
| 2014/0163333 A1 | 6/2014 | Horseman |
| 2015/0186609 A1 | 7/2015 | Utter, II |
| 2015/0305675 A1 | 10/2015 | Miller et al. |
| 2016/0161254 A1 | 6/2016 | Nakajima et al. |
| 2016/0317089 A1 * | 11/2016 | Fyfe ............... A61B 5/7455 |
| 2017/0000386 A1 | 1/2017 | Salamatian et al. |
| 2018/0021210 A1 | 1/2018 | Stray-Gundersen et al. |
| 2018/0032944 A1 | 2/2018 | Sarvana et al. |
| 2018/0261309 A1 * | 9/2018 | Vasiliu-Feltes ........ G16H 50/70 |
| 2019/0015046 A1 | 1/2019 | Whitehouse et al. |
| 2019/0132948 A1 | 5/2019 | Longinotti-Buitoni et al. |
| 2019/0183412 A1 | 6/2019 | Huijbregts et al. |
| 2019/0234817 A1 | 8/2019 | Sun |
| 2019/0265270 A1 | 8/2019 | Yamashita et al. |
| 2019/0300964 A1 | 10/2019 | Zhang et al. |
| 2020/0097329 A1 | 3/2020 | Zhou et al. |
| 2020/0342608 A1 | 10/2020 | Lamichhane et al. |
| 2021/0169417 A1 * | 6/2021 | Burton ............... A61B 5/4857 |

\* cited by examiner

METHOD AND SYSTEM FOR MONITORING CORE BODY MOVEMENTS

CROSS-REFERENCE TO RELATED APPLICATIONS

This application is a continuation of U.S. application Ser. No. 16/622,671, filed Dec. 13, 2019, which is a U.S. National Stage application under 35 U.S.C. § 371 of International Application PCT/AU2018/050600, filed Jun. 18, 2018, which claims the benefit of priority to Application AU 2017902302, filed Jun. 16, 2017. Benefit of the filing date of each of these prior applications is hereby claimed. Each of these prior applications is hereby incorporated by reference in its entirety.

FIELD OF THE INVENTION

The present invention relates to a method and system for monitoring core body movements.

BACKGROUND

Physically demanding jobs expose workers to prolonged manual handling activities, such as lifting, holding or moving loads. These manual handling activities can lead to negative health effects and manual handling injuries, such as back pain. The effect of manual handling injuries caused through instantaneous injuries or by gradual wear and tear, has a significant social, human and organisational cost for both workers and workplace organisations.

Workplace organisations have duties to protect workers from the risk of manual handling injuries. These duties include identifying tasks that involve hazardous manual handling, assessing the risk of these tasks, and reducing or eliminating the risks through risk control mechanisms.

Risk control mechanisms may be in the form of training programs for educating workers about proper manual handling practices, training manuals for referencing, and mechanical aids for reducing physical efforts. However, the implementation of risk control mechanisms does not ensure the elimination of manual handling injuries. Once implementation has occurred, continuous monitoring of worker habits and adoption of the risk control mechanisms is necessary.

Safety officers are typically employed to monitor worker habits and their adoption of the risk control mechanisms. These safety officers are required to warn workers when they are exercising poor manual handling practices, provide re-education when workers revert to poor manual handling practices, and report incidents to the organisation. However, safety officers may not be present or made aware of incidents where workers exhibit poor manual handling practices and/or incur a manual handling injury.

The present invention seeks to overcome, or at least substantially ameliorate, the disadvantages and shortcomings of the background art.

Any references to documents that are made in this specification are not intended to be an admission that the information contained in those documents form part of the common general knowledge known to a person skilled in the field of the invention, unless explicitly stated as such.

In this specification the terms "comprising" or "comprises" are used inclusively and not exclusively or exhaustively.

SUMMARY OF THE INVENTION

According to a first aspect of the invention, there is provided a system for monitoring core body movement, comprising:
  a sensor device for collecting a data set representing a plurality of core body movements over time from a monitoring device;
  a processor for determining a plurality of risk scores from the data set; and an output device for indicating the risk scores.

In an embodiment the monitoring device is a single device used at a time for the or each user and the collection of data is from the single monitoring device only.

In an embodiment of the invention, the data set representing body movements comprises a back bending angle and a torso twisting angle of each movement.

In an embodiment of the invention, the bending angle is measured by the change in angle relative to horizontal in respect of a first reference point on a user's back. The horizontal is measured by the monitoring device and the reference point is determined from the position of the monitoring device on the user's torso.

In an embodiment of the invention, the twisting angle is measured by the change in horizontal position of the first references point so as to determine an angle relative to vertical relative to a second reference point on the user's back. In an embodiment, the vertical is taken to coincide with a line of gravitational force.

In an embodiment of the invention, the data set representing body movements further comprises a static posture time of each movement.

In an embodiment of the invention, the static posture time is the time during which substantially no movement of the first reference point and the second reference point on the user's back occurs.

In an embodiment of the invention, the processor for collecting the data set is configured to add data to the data set each time a pre-set time interval has passed.

In an embodiment of the invention, the processor for determining the plurality of risk scores comprises a processor for determining a set of risk factor coefficients based on body movements.

In an embodiment of the invention, the risk factor coefficients comprise a value determined by a combination of the bending angle and the twisting angle.

In an embodiment of the invention, the risk factor coefficients comprise a value determined by the static posture time. For example, seconds in an awkward posture.

In an embodiment of the invention, the risk factor coefficients comprise a value determined by activity frequency. In an embodiment the activity is bending, twisting, or both.

In an embodiment of the invention, the risk factor coefficients comprise a value determined by a duration of rest. For example, minutes before next activity.

In an embodiment of the invention, the risk factor coefficients comprise a value determined by a duration of activity before rest. For example, hours of activity before a rest.

In an embodiment of the invention, the risk factor coefficients comprise a value determined by the amount of exertion in an or each activity. For example, intensity of a lift.

In an embodiment of the invention, the risk factor coefficients comprise a frequency of activity in a given time. For example, number of lifts per minute.

In an embodiment of the invention, the risk factor coefficients comprise a value determined by the amount of exertion in an or each activity.

In an embodiment of the invention, the risk factor coefficients comprise a value determined by one or more of the following: the amount of time taken to bend down; the amount of time to bend up, the jerkiness of a movement, the angle of the torso at the end of the movement, the smoothness of acceleration through the movement, the area under a curve mapping an angle of bending of a movement over time, and the sum of acceleration of a movement over time.

In an embodiment of the invention, the system comprises a device for indicating a meaning of the risk score. In an embodiment when the risk score reaches a threshold it is interpreted to mean that a movement is of high risk and the number of high risk movements is recorded. In an embodiment the device for indicating the risk scores comprises a device for indicating reaching of a threshold.

In an embodiment of the invention, the output indicating the risk scores or the means reaching of a threshold comprises a visual indicator.

In an embodiment of the invention, the output indicating the risk scores or the means reaching of a threshold comprises a tactile indicator.

In an embodiment of the invention, the output indicating the risk scores or the means reaching of a threshold contains an audio indication.

In an embodiment of the invention, the system further comprises transmitter for transmitting a signal.

In an embodiment of the invention, the signal comprises the data set.

In an embodiment of the invention, the signal comprises the plurality of risk scores or the meaning of the risk scores or the reaching of a threshold, or combinations of these.

In an embodiment the signal comprises the quantity of high risk movements.

In an embodiment of the invention, the system further comprises processor for determining a risk threshold of a user of the monitoring device using the plurality of risk scores and indicating to the user if the risk threshold has been reached.

In an embodiment of the invention, the system further comprises an output for indicating to the user that the risk threshold has been reached. In an embodiment the system further comprises an output for communicating that the amount of high risk movements should be reduced.

In an embodiment of the invention, the processor for determining the plurality of risk scores is configured to analyse the data set to determine a period of activity before rest.

In an embodiment of the invention, the processor for determining the plurality of risk scores is configured to analyse the data set to determine the period of activity before rest is determined by determining the period over which one or more activities occur before a prolonged period without activity occurs.

In an embodiment of the invention, the processor for determining the plurality of risk scores is configured to analyse the data set to determine a period of rest, wherein the period of rest comprises the duration of a period in which no activity occurs.

In an embodiment of the invention, the processor for determining the plurality of risk scores is configured to analyse the data set to determine an amount of exertion.

In an embodiment of the invention, the processor for determining the plurality of risk scores is configured to determine the amount of exertion by determining a period of time at which the user is bending or twisting, or both. In an embodiment of the invention, the determined amount of exertion is used to calculate an inferred weight being handled by the user.

In an embodiment of the invention, the risk scores are progressively determined over time.

In an embodiment of the invention, the risk factor coefficients are progressively determined over time, by cumulative analysis of the data set over a working period, such as for example, over the working day.

According to a second aspect of the invention, there is provided a system for monitoring core body movement, comprising:
  a means for collecting a data set representing core body movements over time from a monitoring device;
  a means for determining a plurality of risk scores from the data set; and
  a means for indicating the risk scores or indicating high risk movements.

In an embodiment the means for collecting collects the data set so as to comprise a plurality of core body movements over a period of time which comprises at least two movements before a rest.

According to a third aspect of the invention, there is provided a system for monitoring core body movement comprising;
  means for collecting a data set representing a plurality of core body movements over time from a monitoring device;
  means for determining a plurality of risk scores based on the data set;
  means for determining when a risk score exceeds a risk threshold; and
  means for indicating to a user of the monitoring device when the risk threshold has been reached.

In an embodiment, indicating to the user of the monitoring device when the risk threshold has been reached comprises indicating when a movement is high risk and/or indicating to the user the number of high risk movements.

According to a fourth aspect of the invention, there is provided a system for monitoring core body movement, comprising:
  a sensor device for collecting a data set representing a plurality of core body movements over time from a monitoring device;
  a processor for determining a plurality of risk scores from the data set; and
  a processor for determining when a risk score exceeds a risk threshold; and
  an output device for indicating to a user of the monitoring device when the risk threshold has been reached.

According to a fifth aspect of the invention, there is provided a system for monitoring core body movement comprising:
  means for collecting a plurality of data sets representing a plurality of core body movements over time from a plurality of monitoring devices;
  means for determining a plurality of risk scores for each monitoring device based on the plurality of data sets from each monitoring device;
  means for aggregating the plurality of risk scores from each monitoring device into a report; and
  means for indicating the report.

According to a sixth aspect of the invention, there is provided a system for monitoring core body movement comprising:

a sensor device for collecting a plurality of data sets representing a plurality of core body movements over time from a plurality of monitoring devices;

a processor for determining a plurality of risk scores for each monitoring device based on the plurality of data sets from each monitoring device;

a processor for aggregating the plurality of risk scores from each monitoring device into a report; and an output device for indicating the report.

According to a seventh aspect of the invention, there is provided a method for monitoring core body movement, comprising:

collecting a data set representing a plurality of core body movements over time from a monitoring device;

determining a plurality of risk scores from the data set;

determining a level of risk from the plurality of risk scores; and indicating the level of risk.

According to an eighth aspect of the invention, there is provided a monitoring device for monitoring core body movement, comprising:

at least one sensor positioned to sense a plurality of core body movements over time;

a storage device configured to store the data set; and a communication device for transmitting the data set.

In an embodiment of the invention, the monitoring device further comprises an indicator for providing an indication of a level of risk.

According to a ninth aspect of the invention, there is provided a computer program product, comprising a set of instructions for controlling a processor to:

retrieve a data set representing a plurality of core body movements over time from a monitoring device;

determine a plurality of risk scores based on the data set;

determine a level of risk from the plurality of risk scores; and indicate the level of risk.

According to a tenth aspect of the invention, there is provided a computer program product, comprising a set of instructions for controlling a processor to:

retrieve a plurality of data sets representing a plurality of core body movements over time from a plurality of monitoring devices;

determine a plurality of risk scores for each monitoring device based on the plurality of data sets from each monitoring device;

aggregate the plurality of risk scores from each monitoring device into a report; and indicate the report.

According to an eleventh aspect of the invention, there is provided a computer program product, comprising a set of instructions for controlling a processor to:

retrieve a data set representing a plurality of core body movements over time from a monitoring device;

determine a plurality of risk scores based on the data set;

determine when a risk score exceeds a risk threshold; and transmit instructions to the monitoring device to indicate to the user that the risk threshold has been reached.

BRIEF DESCRIPTION OF THE DRAWINGS

Embodiments of the present invention are described in the following detailed description by example only, with reference to the following drawings.

DETAILED DESCRIPTION OF EMBODIMENTS OF THE INVENTION

A worker may not be aware that they are exhibiting poor manual handling practices, such as a poor lifting posture, a high frequency of lifts during a work shift, carrying a load for an extended period, not taking a rest after exertions, and not resting for long enough. For a worker to reduce the risk of injury, continuous monitoring of the core body movements can be conducted and a data set representing the movements can be measured and stored for analysis. Additionally, the data set can be analysed and a resultant report can be made available for the worker and an employment organisation to understand the worker's manual handling practices. Furthermore, the data set may be analysed to determine whether a hazardous practice threshold has been reached, wherein the worker may be warned to cease or correct a dangerous manual handling action.

Figure 1:
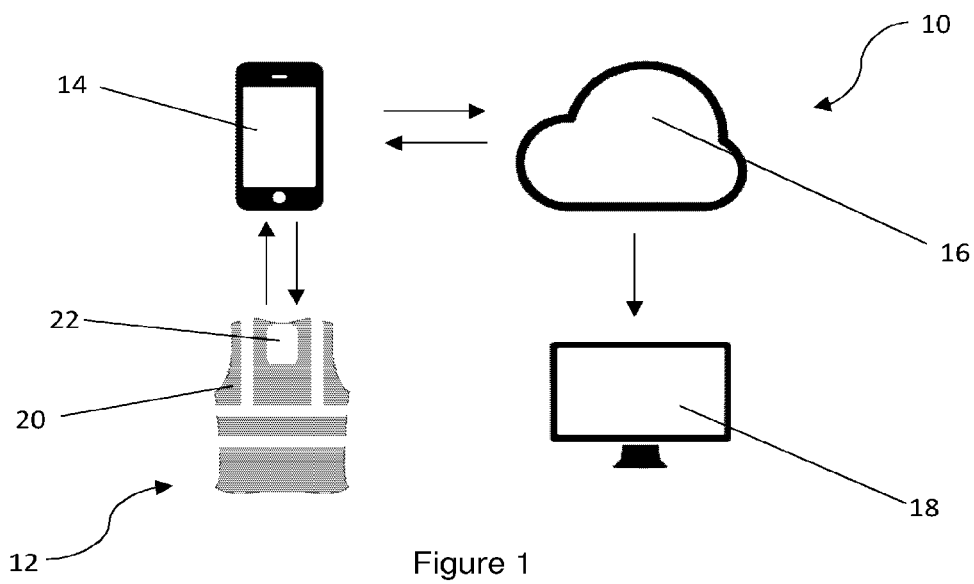
FIG. 1 illustrates an example of a system embodying the present invention.
Figure 2A:
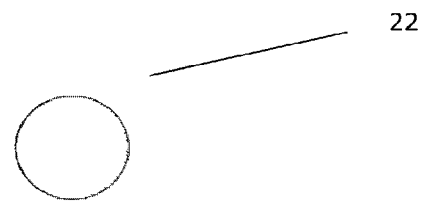
FIG. 2A is a schematic view of an alternative clip-on type of monitoring device of the system of FIG. 1.

FIG. 1 illustrates a system 10 for monitoring the core body movements of a user. The system 10 comprises a wearable item 12 that is worn by a user and which is able to communicate with a personal computing device 14 that is able to connect to and communicate with a remote computing resource 16, and in an embodiment a remote computing device 18. The wearable item 12 shown in FIG. 1 is a vest, however in an alternative, the wearable item is a clip-on tag that attaches to the user or their clothing as depicted in FIG. 2A. The wearable item 12 comprises a monitoring device 22 for collecting a data set representing body movement of the user over time. The wearable item is for attaching the monitoring device 22 to the user and could take on other forms, such as for example, a strap. Each of the computing devices 14, 18 can be a smartphone, a tablet computer, a laptop computer, a desktop computer or the like. The remote computing resource 16 can be a network based (cloud) computer, a remote computer, or a remote server. The remote computing resource 16 can be implemented using any suitable computing device, preferably one with more processing power than the computing devices 14, 18.

Figure 2B:
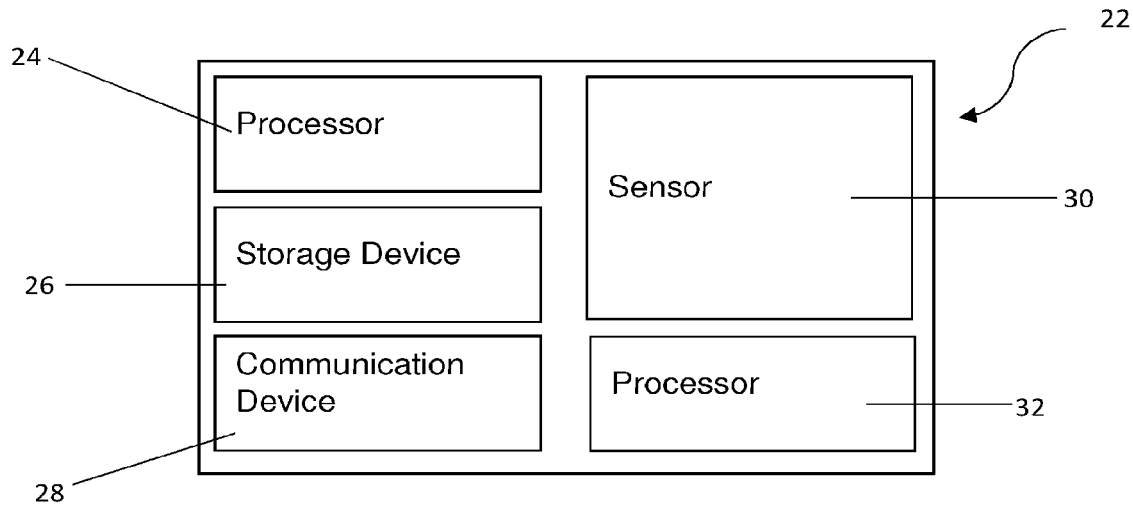
FIG. 2B is a block diagram of components of a monitoring device of the system of FIG. 1.

Referring to FIG. 2B, the monitoring device 22 comprises components including a processor 24, a storage device 26, a communication device 28 and one or more sensors 30 for determining movement of the core body of a user. The processor 24 may comprise a data storage device for storing working data and operating instructions, and may be in the form of non-volatile solid state memory or similar. The storage device 26 comprises a short term storage for storing data from the sensor 30 and/or processed data from the processor 24, and may be in the form of RAM, solid state memory or similar.

The processor 24 may comprise one or more physical, logical or virtual CPUs and is for executing the operating instructions, in the form of a computer program, so as to control the components to operate as the monitoring device 22, as described further below. The instructions may be in the form of firmware, or electronic circuitry, or embedded software, as appropriate and/or convenient. In a preferred form, the components of the monitoring device 22 are low power drawing devices that are powered by a long life battery.

Figure 5:
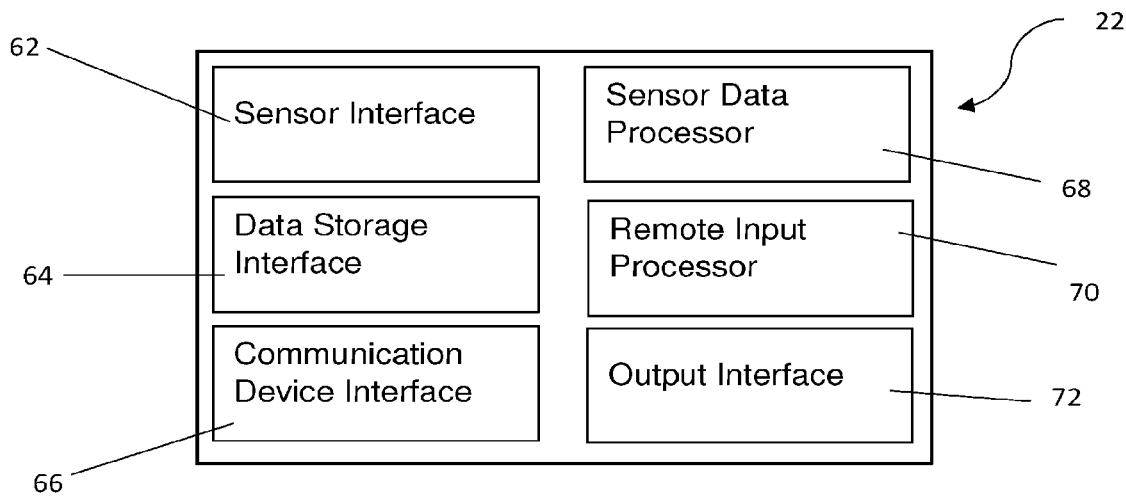
FIG. 5 is a block diagram of functional modules of the monitoring device of FIG. 2.

The processor 24 may be configured by operating instructions to operate as one or more of the functional modules described in relation to FIG. 5. The functional modules may also, in addition or instead, and as appropriate and/or convenient, be formed of electronic circuitry. The communication device 28 is typically a wireless network interface, such as a Bluetooth transceiver. Other types of interface are possible, such as IEEE 802.11.

The monitoring device 22 may also comprise a processor 32 for analysing the data set from the sensor 30 to determine when an action or set of actions reaches a safety threshold(s), in which case the user may be alerted. The processor 32 may make a similar analysis to that performed by the remote computing resource 16, as described below, or it may be a simplified version of the analysis. The processor 32 may be a separate processor to processor 24, in a physical, logical, or functional sense, or the processor 24 may be configured to operate as the processor 32.

Figure 3:
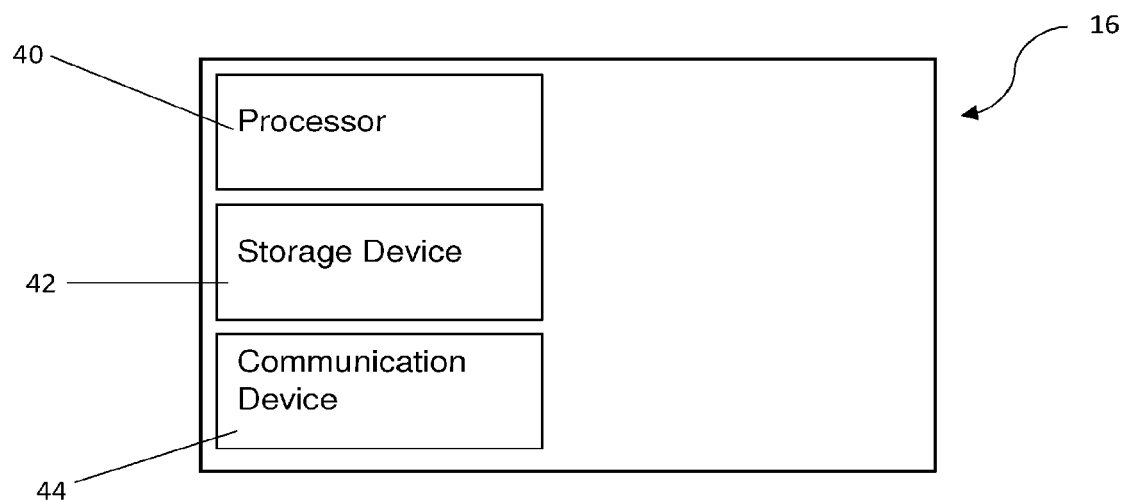
FIG. 3 is a block diagram of components of a remote computing resource of the system of FIG. 1.

Referring to FIG. 3, the remote computing resource 16 comprises components including a processor 40, a storage device 42, and a communication device 44. The processor 40 may comprise a data storage device for storing working data and operating instructions, and may be in the form of non-volatile solid state memory or similar. The storage device 42 comprises a long term storage for non-volatile storing of data received via the communication device 44 or processed data from the processor 40. The storage device 42 may be in the form of non-volatile solid state memory, hard disk drive(s) or similar.

The processor 40 may comprise one or more physical, logical or virtual CPUs and is for executing the operating instructions, in the form of a computer program, so as to control the components to operate as the remote computing resource 16, as described below. The instructions may be in the form of firmware, or electronic circuitry, or software, as appropriate and/or convenient.

Figure 6:
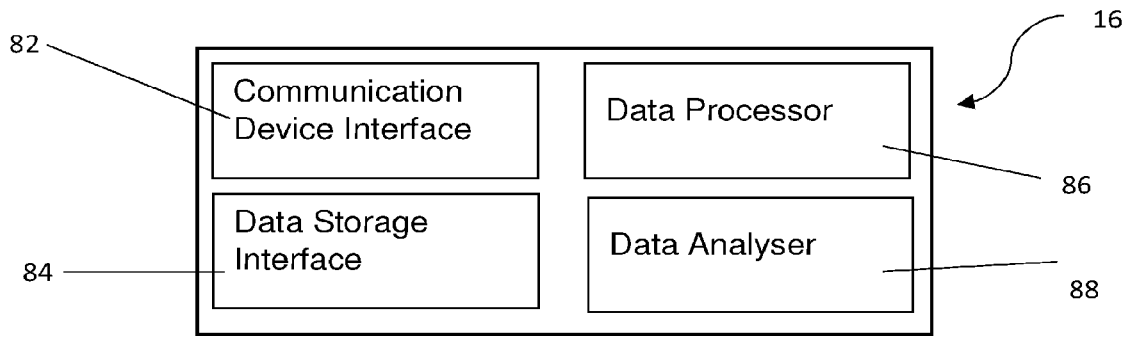
FIG. 6 is a block diagram of functional modules of the remote computing resource of FIG. 3.

The processor 40 may be configured by operating instructions to operate as one or more of the functional modules described in relation to FIG. 6. The functional modules may also, in addition or instead, as appropriate and/or convenient, be formed of electronic circuitry. The communication device 44 is a computer network interface.

Figure 4:
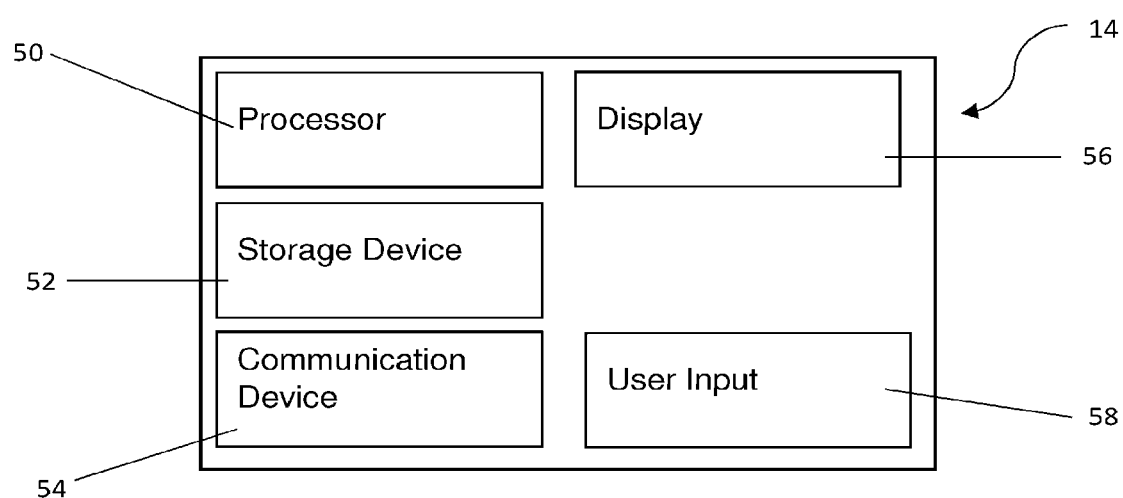
FIG. 4 is a block diagram of components of a personal computing resource of the system of FIG. 1.

Referring to FIG. 4, the personal computing device 14 comprises components including a processor 50, a storage device 52, a communication device 54, a display 56 and a user input 58, such as a touch screen. The processor 50 may comprise a data storage device for storing working data and operating instructions, and may be in the form of non-volatile solid state memory or similar. The storage device 52 comprises a long term storage for non-volatile storing of data received via the communication device 54 or processed data from the processor 50, and the storage device 42 may be in the form of non-volatile solid state memory or similar.

The processor 50 may comprise one or more physical, logical or virtual CPUs and is for executing the operating instructions, in the form of a computer program, so as to control the components to operate as the personal computing device 14, as described below. The instructions may be in the form of firmware, or electronic circuitry, or embedded and/or installed software, as appropriate and/or convenient.

Figure 7:
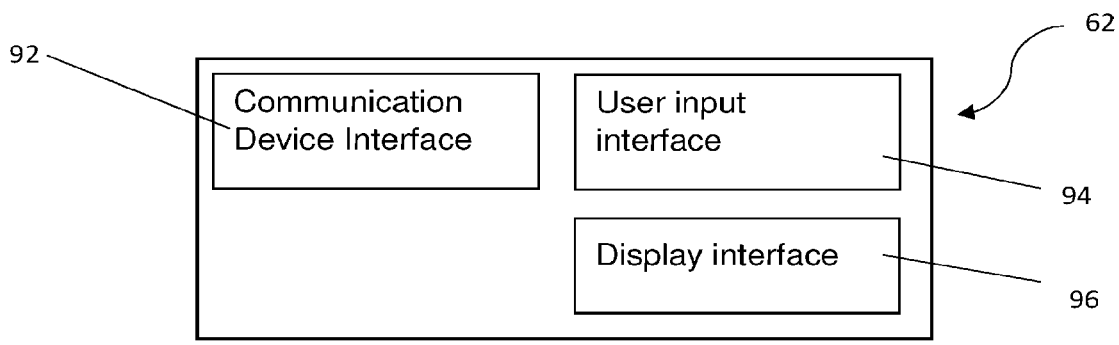
FIG. 7 is a block diagram of functional modules of the personal computing resource of FIG. 4.

The processor 50 may be configured by operating instructions of an application computer program to operate as one or more of the functional modules described in relation to FIG. 7. The functional modules may also, in addition or instead, as appropriate and/or convenient, be formed of electronic circuitry. The communication device 54 is typically a cellular telephone network interface and/or a Wi-Fi interface and/or a Bluetooth interface.

Referring to FIG. 5, the monitoring device 22 comprises functional modules including a sensor interface 62, a data storage interface 64, a communication device interface 66, a sensor data processor 68, a remote input processor 70 and an output interface 72. The sensor interface 62 takes a raw sensor input signal from the sensor 30 and provides it as sensor data to other functional modules, such as the data storage interface module 64 which stores the sensor data in the storage device 26. The sensor data processor 68 is arranged to access sensor data from the sensor 30 via the sensor interface 62, and/or to retrieve data from the storage device 26 via the data storage interface 64. Data from the remote computing resource 16 may be received via the communication device interface 66. This data may be stored in the storage device 26 via the data storage interface 64. It may also be processed by the remote input processor 70. Data may be output to the personal computing device 14 (and then in turn to the remote computing resource 16) via an output interface 72.

Referring to FIG. 6, the remote computing resource 16 functional modules include a communication device interface 82, a data storage interface 84, a data processor 86, and a data analyser 88. The communication device interface 82 is arranged to send and receive data to/from the personal computing device 14 or the remote computing device 18. The data storage interface 84 stores the sensor data in the storage device 42. The data processor 86 is arranged to access stored data from data storage device 42 via the data storage interface 84. Typically the processing involves determining the risk factors, as described below. The determined risk factors may then be stored in the data storage device 42 via the data storage interface 84. The data analyser 88 is arranged to access stored data from data storage device 42 via the data storage interface 84, or the risk factors data from the data processor 86 to analyse it. Typically the analysis involves determining whether one or more of the risk factors reach a threshold, as described below. Risk factor data or threshold comparison data may be output to the personal computing device 14 (and then in turn to the monitoring device 22) via a communication device interface 82.

Referring to FIG. 7, the personal computing device 14 comprises functional modules including a communication device interface 92, a user input interface 94, and a display interface 96. The communication device interface 92 is arranged to send and receive data to/from the monitoring device 22 or the remote computing device 18. The user input interface 94 receives inputs from the user. The display interface 96 provides information to the user.

The steps of the method of monitoring the core body movements of a user may be implemented by the monitoring device 22, personal computing device 14 and remote computing resource 16 operating by, for example, their respective processors 24, 40 and 50 executing respective instructions of a respective computer program so as to operate as described further below.

In an embodiment, the measurement device collects a data set representing body movement over time of a user. The personal computing device 14 relays the data set to the remote computing resource 16 which analyses the data set to determine a plurality of risk scores. The risk scores are collated to produce an indication of the level of risk for incurring injury in the manual handling activities in which the user has been or is currently subjected to. The indication of the level of risk may be the number of high risk movements in a given period. The indication of the level of risk is transmitted to the personal computing device 14, which delivers the indication to the user. The personal computing device 14 may transmit the indication of the level of risk to the wearable item 12 for it to deliver the indication to the user.

In a preferred embodiment, the indication is a visual indication. The visual indication may be in the form of a graph indicating the plurality of risk scores plotted over a collection time frame of the data set. In another embodiment, the visual indication is in the form of a written report which may include the visual graph. In a further embodiment, the visual indication is in the form of lights which signify various risk levels. In an embodiment the visual indication may be the number of high risk movements in a given period (eg per hour or per work shift).

In other embodiments of the invention, the indication may be an audio indication or a tactile indication. The audio indication is preferably in the form of an aural report, providing information and alerts to the user. In another embodiment, the audio indication is in the form of a tone that may notify a user of various risk levels based upon volume and repetitions. The tactile indication is preferably in the form of a single vibration or a series of vibrations that may notify a user of various risk levels based upon intensity and repetitions.

In an embodiment of the invention, the remote computing resource 16 is a network based (cloud) computer configured to determine whether a risk score determined from the data sets has exceeded a risk threshold. The risk threshold is a determined value that indicates when the user is participating in a manual handling activity that has the potential to cause serious injury. If the risk threshold has been exceeded, the remote computing resource 16 will generate an alert which is transmitted to the personal computing device 14 and to the wearable item 12. The alert is in the form of a noticeable indication, such as an alarm tone from the speakers of the personal computing device 14 or vibrations from the monitoring device 22 of the wearable item 12.

In another embodiment of the invention, the system 10 comprises a plurality of wearable items 12 which collect a plurality of data sets representing body movements over a period of time from a plurality of users. The plurality of data sets is transmitted to a plurality of personal computing devices 14, which are each connected to the remote computing resource 16. The remote computing resource 16 is configured to receive the plurality of data sets and analyses each data set separately to determine a plurality of risk scores for each data set. The plurality of risk scores is collated to produce a plurality of indicators of the level of risk for incurring injury for each data set. The indicator of level of risk may be the number of high risk movements in a time period. Each indication of the level of risk is transmitted to each personal computing device 14 for delivery to each user. Each personal computing device 14 may transmit the indication to each wearable item for delivery to each respective user.

The remote computing device 18 is configured to receive an aggregated report from the remote computing resource 16. In an embodiment the aggregated report is created by the remote computing resource 16 by collating information gathered by the data sets and the plurality of risk scores.

FIG. 1 shows the wearable item 12 in the form of a vest 20, covering the torso of the user, having a monitoring device 22. As noted above, a preferred alternative to the vest is a clip-on tag, as depicted in FIG. 2A. The monitoring device 22 is integrated into the back of the vest 20 with a patch. However, the monitoring device 22 may be integrated into the vest 20 using any other conventional means and may be positioned at any suitable location on the torso. Additionally, the wearable item 12 may be in the form of any wearable piece of clothing or a cover that is worn on the torso of the user. The monitoring device 22 may transmit measurement data to the computing device 14 by a direct connection, such as a Bluetooth wireless connection, or other suitable connection, or it may be relayed to the computing device 14 via a receiver device, such as a Bluetooth beacon. Notably the monitoring device 22 is in a single package located on the torso. This is notably distinct from the two (or more) monitoring devices at spaced apart locations on the body. The monitoring device 22 may work in combination with another monitoring device, which might provide an enhancement to the monitoring described herein, but the monitoring described herein does not require another monitoring device for sensing movement etc of the body.

In the present invention, the at least one sensor comprises a multi-axis accelerometer, capable of detecting magnitude and direction of acceleration in order to determine core body movements of the user, and preferably including bending and twist of the back of the user. However, additional sensors such as gyroscopes, magnetometers, or further accelerometers may be included in the monitoring device 22 as a sensor array. In an embodiment the accelerometer is sampled by the sensor interface 62 when a substantial change in acceleration is experienced by the accelerometer. This can conserve battery life. In addition, or instead, the accelerometer is sampled by the sensor interface 62 after period of time has lapsed, such as for example 20 ms (producing a sampling rate of 5 Hz). In a preferred form the sample rate is about 1.25 Hz in sleep mode and 52 Hz in active mode.

As the at least one sensor 30 measures the movement of the core body, the processor 24 processes the measurements of core body movements. In an embodiment the core movements are determined to be action and its parameters, which for example include the maximum angle of bending and the maximum angle of twisting in the action. It may also determine a duration of motion in the action, and one or more durations of stages of movement in the action. These are determined, collected and stored in the storage device as the data set. In an embodiment, periodically the data set can be transmitted, in the form of a signal, to an external source. The process will repeat according to a pre-set time interval. The time interval may be altered according to instructions from the user or from an external source, such as the remote computing resource 16.

The data set comprises values corresponding to specific core body movements. The primary core body movements are angular movements in a vertical plane, and rotational movements. These movements are used to determine a bending angle and a twisting angle of the user's torso, which provides information regarding trunk flexion/extension and rotation. The bending angle is measured by the change in angle relative to the horizontal of a first reference point, indicating the neutral stance of the user. The twisting angle is measured by the change in angle relative to a line of gravitational force of a second reference point, indicating the neutral stance of the user. The data set further comprises values relating to the static posture time. The static posture time is the time during which substantially no movement of the first and second reference points occurs.

The monitoring device 22 is configured to transmit the data sets to external sources, such as the personal computing device 14. In the present invention, the monitoring device 22 will automatically transmit the data sets when within range of the personal computer device 14. However, the transmission of the data sets may occur according to specific instructions or prompts. In an example, the monitoring device 22 may transmit the data sets to the personal computing device 14 upon receiving a broadcast from an electronic beacon, such as a Bluetooth low energy beacon. In a further example, the monitoring device 22 may transmit the data sets to the personal computing device 14 upon receiving instructions from the personal computing device 14. In another embodiment, the monitoring device 22 may be configured to transmit the data set to the remote computing resource 16.

In the current invention, the monitoring device 22 is configured to provide means of indications to the user. The means of indications are used to indicate to the user the indications of the levels of risk determined by the remote computing resource 16, or the alert generated by the remote computing resource 16. The means of indications may be in the form of a speaker and/or a vibration device.

The monitoring device 22 may be ruggedized to suit the environment in which it will be operating.

The personal computing device 14 is preferably configured to remain in continuous or frequent connection with the monitoring device 22, so to receive the data sets from the wearable item 12. Alternatively, the monitoring device 22 will choose when to connect to the personal computing device 12. This may be periodically, or at the conclusion of each or a number of exertions. In another alternative, the personal computing device 14 will initiate connection to the monitoring device when the user interacts with the device 14, whereupon stored data since the last download will be transmitted to the personal computing device 14. In the present invention, the personal computing device 14 is used as part of a relay network to transmit, in the form of a signal, the data sets from the monitoring device 22 to the remote computing resource 16 and instructions from the remote computing resource 16 to the monitoring device 22. The personal computing device 14 is further configured to receive the plurality of risk scores and associated indications of levels of risk. The plurality of risk scores and the indications of levels of risk are stored on a storage device of the personal computing device 14 and may be displayed to the user for reference of their manual handling activities.

In an embodiment of the invention, the personal computing device 14 is further configured to receive the alert generated from the remote computing resource 16 for transmitting to the wearable item 12 and to indicate to the user of their participation in a manual handling activity that has the potential to cause severe injury. The indication issued by the personal computing device 14 may be in the form of a visual alert, an audio alert, and/or tactile feedback.

In an embodiment of the invention, the personal computing device 14 is further configured to transmit location data and/or other identification data with the data set to the remote computing resource 16.

In the present invention, the remote computing resource 16 is configured to receive and analyse the data set from the wearable item 12 to determine a plurality of risk scores.

The analysis comprises assigning a plurality of risk factor coefficients to the information found in the data sets. The risk factor coefficients are comprised of values determined by the combination of the bending angle/twisting angle, the static posture time, an amount of exertion, a period of exertion, a period of rest, and a period without rest. An action is defined as any collected values of significant magnitude from the first and second reference points in which the posture is non-neutral. The amount of exertion is determined by the magnitude of deviance from the first and second reference points. The period of an action is determined by the time frame in which exertion is determined to have occurred. The period of rest is determined by the time period between actions, or if actions are repeated frequently a prolonged period between when the last action occurred and when a new set of actions is commenced. The period without rest is determined by the time period between rests.

The risk factor coefficients are used as input into a calculation, resulting in a risk score representing the level of risk at a current state of time. The resultant plurality of risk scores is collated to provide an indication of the level of risk of the current activities. Additionally, each risk score is compared to the risk threshold value, which will result in the generation of the alert. The remote computing resource 16 is further configured to transmit the plurality of indications of the level of risk and the alerts to the wearable item 12 and the personal computer device 14.

The remote computing resource 16 is further configured to receive a plurality of data sets from a plurality of wearable items 12 to analyse and determine a plurality of risk scores for the user of each wearable item 12. The remote computing resource 16 will subsequently aggregate the plurality of risk scores for each wearable item 12 to produce an aggregated report that is transmitted to the remote computer 18. The remote computer 18 is typically the computer assigned to a safety officer or other workplace official that monitors workplace safety. In the present invention, the aggregated report provides a general indication of the levels of risk associated to the workers from the workplace organisation and/or from specific departments/sections of the workplace organisation. However, the aggregated report may include detailed information of individual users and their activities as required.

In an embodiment of the invention, the aggregated report may include additional information, such as location data and/or identification data to provide relevant information to the general indication of the levels of risk. In an example, the aggregated report may combine location data with the general indication of the levels of risk to determine workplaces with higher occurrences of dangerous activities.

The remote computing resource 16 is controlled by a computer program executable by a computer of the remote computing resource 16 embodied on a computer readable media. The computer program comprises instructions to configure the remote computing resource 16 as a special purpose machine that performs the functions previously described.

The personal computer device 14 is intended to be arranged as part of the system 10 which includes the monitoring device 22 and the remote computing resource 16. However, in an embodiment of the invention, the system may be comprised only of the monitoring device 22 and the personal computer device 14. In this embodiment, the personal computer device 14 is configured to perform the functions of the remote computing resource 16 in addition to its own functions.

The monitoring device 22 is intended to be arranged as part of the system 10, which includes the personal computer device 14 and the remote computing resource 16. However, in an embodiment of the invention, the monitoring device 22 may be configured to perform part of the functions of the remote computing resource 16 in order to consistently generate the alert of dangerous manual handling activities.

In an embodiment of the invention, the monitoring device 22 may be configured to perform the functions of the remote computing resource 16.

Figure 8:
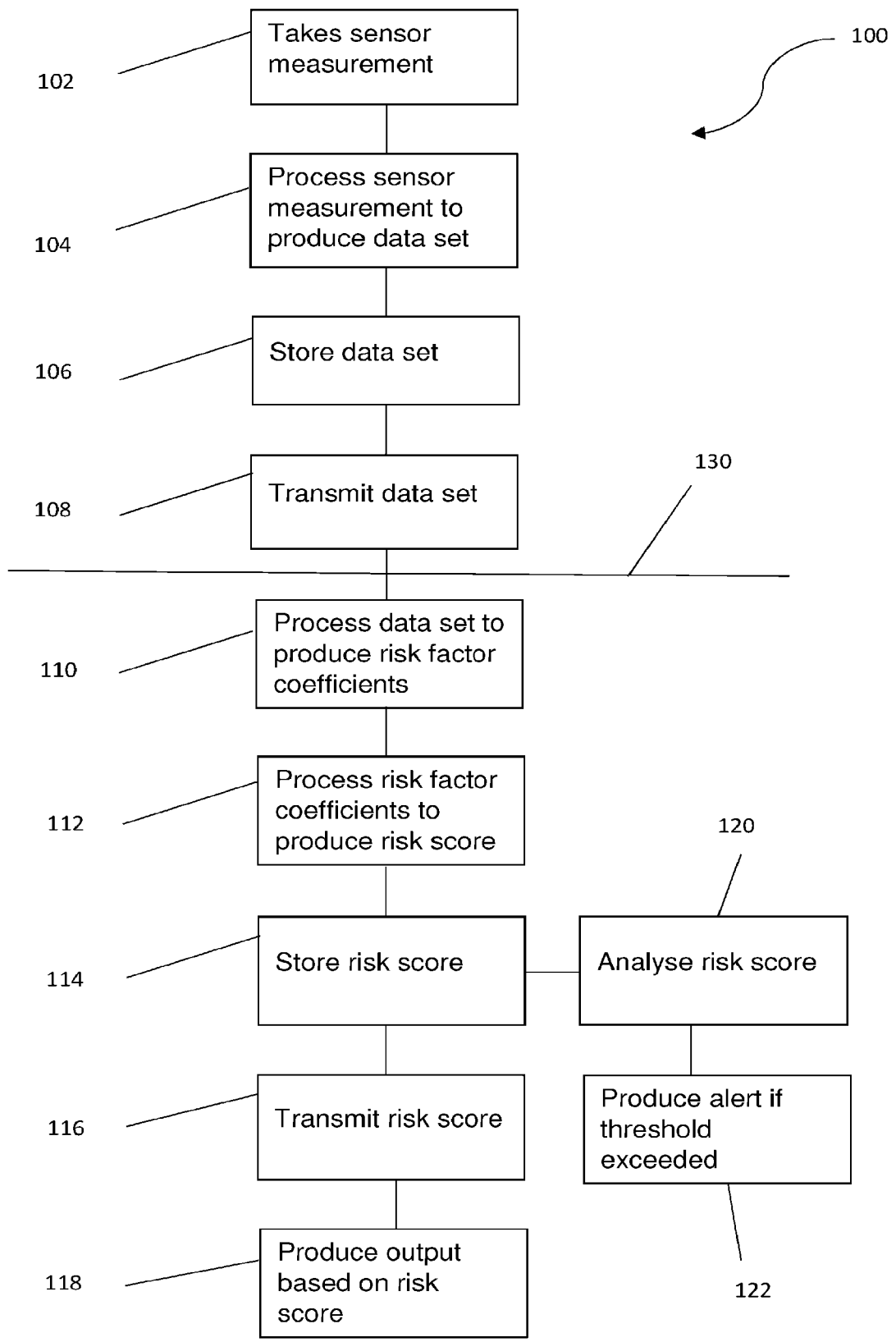
FIG. 8 is a flowchart illustrating a method of monitoring core body movement.

A method of operation 100 and use of the system 10 used to monitor the core body movements of the user will now be described in more detail with reference to FIG. 8.

The user wears the monitoring device 22 and conducts the typical manual handling actions required for their job. The monitoring device 22 takes measurements 102. The raw measurements may be processed 104 into a consistent format for a data set representing core body movements as measured by the monitoring device 22 over time. The data set is stored 106 prior to being transmitted 108 to the personal computer device 14 of the user. The data set is stored on the personal computer device 14 prior to transmission to the remote computing resource 16.

The steps above the line 130 are performed by the monitoring device 22. In an embodiment the steps below the line 130 are performed by the remote computing resource 16. However, these steps can be performed by the monitoring device 22.

The data set is processed 110 by the remote computing resource 16 to determine the plurality of risk factor coefficients. The risk scores are calculated 112 using the plurality of risk factor coefficients. The plurality of risk scores are collated into an indication of the level of risk of the manual labour activity prior to transmission 116 to the personal computer device 14 and/or the wearable item 12.

The generation of the alert of engaging in manual handling activity that may potentially lead to injury is initiated by analysis 120 of the plurality of risk scores, such as by comparison against the predetermined risk threshold value by the remote computing resource 16. Alternatively, the number of high risk movements may be compared to a threshold, and if there are too many high risk movements in a given period of time, then an alert is generated. If the risk score exceeds the risk threshold value, the alert is generated 122 by the remote computing resource 16, which transmits the alert to the personal computer device 14 and/or the monitoring device 22. The alert warns the user of their dangerous activity using indications such as visual, aural and/or tactile notifications.

Figure 18:
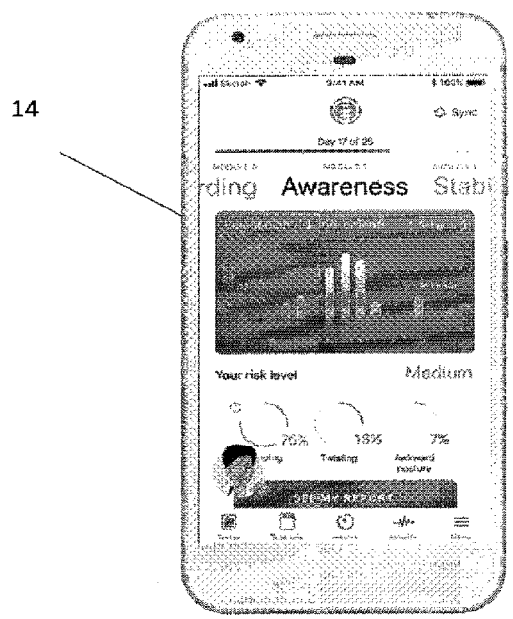
FIG. 18 is a schematic diagram of the display of a report on a portable computing device.

The generation 118 of the aggregate report is initiated by the receipt of the plurality of data sets from the plurality of monitoring devices 22 by the remote computing resource 16. The remote computing resource 16 analyses the plurality of data sets to determine the plurality of risk factor coefficients for each data set. The plurality of risk factor coefficients is subsequently used as input for calculating the plurality of risk scores for each data set. The plurality of risk scores is aggregated into the report providing general information relating to activities of the users of the monitoring devices 22. The report is subsequently transmitted to the remote computer 18 of the safety officer or other official for review and the worker's individual report may be transmitted to their person computing device 14 for inspection of the report as shown in FIG. 18.

In an embodiment, the plurality of risk scores is based on the risk factor coefficients defined as bending coefficient ($K_B$), twisting coefficient ($K_T$), bending/twisting coefficient ($K_{BT}$), continuous duration coefficient ($K_D$), force coefficient ($K_{FO}$), lifting frequency coefficient ($K_{FR}$), rest coefficient ($K_R$), and static posture coefficient ($K_S$).

$K_{BT}$ derived from the bending and twisting angle, according to the formula:

$$K_{BT} = K_B + K_T$$

wherein $K_B$ is the risk factor coefficient for a flexion bending angle (X), as derived below:

$$K_B = 0.480383098521408 \times e^{0.027460952380982X}$$

and $K_T$ is the risk factor coefficient for the twisting angle (Z). In an embodiment, the angle is a bending forward angle. A table reflecting the Bending angle coefficient $K_B$ is below:

TABLE 1

| Coefficient ($K_B$) for bending angle (X) | | | | | | |
|---|---|---|---|---|---|---|
| Bend angle | <30 | <45 | <60 | <75 | <90 | 105 |
| Coefficient | 1.09 | 1.65 | 2.50 | 3.77 | 5.69 | 8.59 |

The value for $K_T$ is dependent upon the twist angle (Z) based on a formula below:

$$K_T = 0.026 * 15.0 * y * (y+1)/2 + 0.32 * y,$$

where y is twisting angle divided by 15.

A table reflecting the Twisting angle coefficient $K_T$ is shown below:

TABLE 2

| Coefficient ($K_T$) for twisting angle (Z) | | | | | | |
|---|---|---|---|---|---|---|
| Twist Angle | <15 | <30 | <45 | <60 | <75 | 90 |
| Coefficient | 0.71 | 1.81 | 3.30 | 5.18 | 7.45 | 10.11 |

In an example, Table 3 demonstrates a range of values for $K_{BT}$ based on various bending and twisting angles.

TABLE 3

| Coefficient ($K_{BT}$) for various bending/twisting angles | | | | | | | |
|---|---|---|---|---|---|---|---|
| Z\X | 0 | 15 | 30 | 45 | 60 | 75 | 90 |
| 30 | 1.09 | 1.80 | 2.90 | 4.39 | 6.27 | 8.54 | 11.20 |
| 45 | 1.65 | 2.36 | 3.46 | 4.95 | 6.83 | 9.10 | 11.76 |
| 60 | 2.50 | 3.21 | 4.31 | 5.80 | 7.68 | 9.95 | 12.61 |

TABLE 3-continued

Coefficient ($K_{BT}$) for various bending/twisting angles

| Z\X | 0 | 15 | 30 | 45 | 60 | 75 | 90 |
|---|---|---|---|---|---|---|---|
| 75 | 3.77 | 4.48 | 5.58 | 7.07 | 8.95 | 11.22 | 13.88 |
| 90 | 5.69 | 6.40 | 7.50 | 8.99 | 10.87 | 13.14 | 15.80 |
| 105 | 8.59 | 9.30 | 10.40 | 11.89 | 13.77 | 16.04 | 18.70 |

For the evaluation of the risk being in an awkward static posture, static posture coefficient $K_{ASP}$ was developed as below:

TABLE 4

Static posture time coefficients

| Time in static | 10 sec | 20 sec | 30 sec | 40 sec | 50 sec | 60 sec |
|---|---|---|---|---|---|---|
| Coefficient | 1.45 | 1.55 | 1.65 | 1.75 | 1.85 | 1.95 |

To reflect difference in risk of high and low intensity movements, intensity coefficient $K_I$ is defined according to whether the intensity is high or low. An example of high intensity is lift with the weight more than 30% of person body mass. The intensity coefficient $K_I$ used is below:

TABLE 5

Intensity coefficients

| Intensity | Low | High |
|---|---|---|
| Coefficient | 1 | 8 |

In an embodiment there are further risk factor coefficients. Risk factor coefficients $K_D$, $K_{FO}$, $K_{FR}$, $K_R$, and $K_S$ are multipliers. In an example, the values for $K_D$, $K_{FR}$, and $K_R$ are shown below.

TABLE 6

Coefficient ($K_D$) for duration of continuous work

| Hours without recovery | 0 | 1 | 2 | 3 | 4 | 5 | 6 | 7 | 8 |
|---|---|---|---|---|---|---|---|---|---|
| Coefficient | 1 | 1.05 | 1.12 | 1.2 | 1.33 | 1.48 | 1.7 | 1.85 | 1.99 |

TABLE 7

Coefficient ($K_{FR}$) for frequency of lifting

| Frequency (lifts/min) | $K_{FR}$ Multiplier |
|---|---|
| <or = 2 | 1.00 |
| 3 | 1.05 |
| 4 | 1.12 |
| 5 | 1.20 |
| 6 | 1.28 |
| 7 | 1.36 |
| 8 | 1.44 |
| 9 | 1.51 |
| 10 | 1.58 |
| 11 | 1.65 |
| 12 | 1.73 |
| 13 | 1.81 |
| 14 | 1.89 |
| >or = 15 | 1.97 |

TABLE 8

Coefficient ($K_R$) for duration of rest between work

| Rest time, minutes | 5 | 10 | 15 | 20 | 30 | 45 | 60 |
|---|---|---|---|---|---|---|---|
| Coefficient | 0.93 | 0.85 | 0.78 | 0.73 | 0.68 | 0.61 | 0.54 |

In an embodiment, the plurality of risk scores is defined as general risk ($R_G$), bending risk ($R_B$), duration risk ($R_D$), force risk ($R_{FO}$), lifting frequency risk ($R_{FR}$), movement risk ($R_M$), static risk ($R_S$), and twisting risk ($R_T$). The plurality of risk scores are used to determine the level of risk in the associated activity, wherein a higher value equates to higher risk.

In an embodiment, the general risk (RG) is derived from the following formula:

$$R_G = R_M \times R_{FR} \times R_R$$

wherein $$R_M = \frac{(K_{BT(1)} \times K_{S(1)} + \ldots + K_{BT(N)} \times K_{F(N)})}{N}$$

$$R_{FR} = \frac{(K_{BT(1)} \times K_{FR(1)} + \ldots + K_{BT(N)} \times K_{FR(N)})}{N}$$

$$R_{FR} = \frac{(K_{BT(1)} \times K_{R(1)} + \ldots + K_{BT(N)} \times K_{R(N)})}{N}$$

N=number of collected data.

In an embodiment, the bending risk ($R_B$), force risk ($R_{FO}$), static risk ($R_S$), and twisting risk ($R_T$) are the following formulae:

$$R_B = \frac{(K_{B(1)} + \ldots + K_{B(N)})}{N}$$

$$R_{FO} = \frac{(K_{BT(1)} \times K_{FO(1)} + \ldots + K_{BT(N)} \times K_{FO(N)})}{N}$$

$$R_S = R_M - R_B - R_F - R_T$$

$$R_T = \frac{(K_{BT(1)} + \ldots + K_{BT(N)})}{N} - R_B$$

The risk coefficients K between 0 angle twisting and 15 degrees twisting, 15 degrees twisting and 30 degrees twisting etc., were counted as 0.026*z+0.32, where z was twisting angle.

In an alternative embodiment, movement risk $R_M$ is calculated as sum of bending, twisting coefficient for corresponding angles multiplied by static coefficient and intensity coefficient, as below:

$$R_M = (K_B + K_T) \times K_{ASP} \times K_I$$

This risk score may be "averaged", as above. The risk score may also be compared to a threshold to determine whether the movement is a "high" risk movement. For example, the threshold may be between 2 and 10, preferably around 2.5 to 5, more preferably about 3.5 to 4, and in an example, 3.77.

Total risk $R_T$ of a plurality of movements over a period of time is calculated as sum of movement risks multiplied by frequency risk, lack of rest risk and recovery coefficient, as follows:

$$R_T = R_M \times K_{FR} \times K_D \times K_R$$

In an embodiment of the invention, $K_{FO}$ is determined from a prediction of a weight class of a lift. The weight class prediction is made based on a weight being lifted in the activity. Preferably the weight classes are divided into light, medium and heavy classes. In an embodiment 'Light' weight lifts have a coefficient multiplier value substantially less than 1. In an embodiment 'Medium' weight lifts have a coefficient multiplier value of about 1. In an embodiment 'Heavy' weight lifts have a coefficient multiplier value substantially more than 1. In an embodiment the risk factor coefficient $K_{FO}$ is determined according to the table shown below.

TABLE 9

Coefficient ($K_{FO}$) for predicted weight class

| Predicted Weight Class | $K_{FO}$ Multiplier |
|---|---|
| Light | 0.5 |
| Medium | 1 |
| Heavy | 1.5 |

In an embodiment, the prediction of the weight class is made by using the recorded raw bending data, which may be a three component time series with a variable sample rate from the 3-axis accelerometer with a time stamp on each sample.

There is also a start time of the event and end time of the event.

Define ACC (acceleration) as an array of shapes (N, 4) defined by the raw data for a detected bending event. The format of ACC may be: [timestamp, aX, aY, aZ], where timestamp is a recorded time of a frame in milliseconds and aX, aY, aZ are X, Y, Z MEMS-type 3-axis accelerometer data in m/s².

From sub-series ACC, bending angle a is calculated by:

$$a = a\tan2(aZ, aY) * \frac{180}{\pi}$$

Figure 13:
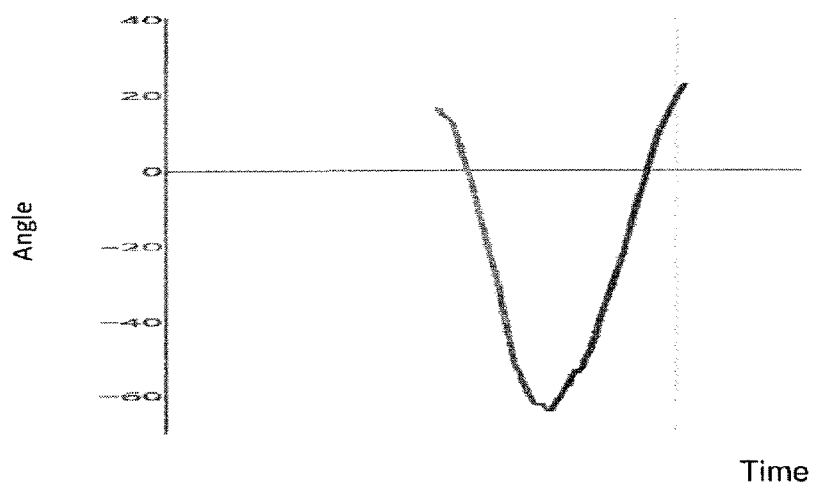
FIG. 13 is a graph of sample numbers against bending angle.

FIG. 13 shows a graph of sample number (x-axis) against bending angle (y-axis).

The bending angle changes over time, and can be divided into three parts of each bend: torso going down, torso almost in the static posture, and torso going up. These durations are used, along with bending angle, and twisting angle as a part of the set of signal features. The descending portion of bending down and the ascending portion is bending up as shown in FIG. 13.

In an alternative intensity can be predicted based on measurement from the measuring device 22. Intensity during the lift is defined as a movement during which high exertion in the human back occurred. As an example of such movement is lifting a heavy box or lifting while person has a back pain. Any such movement is hard for the person and it is usually dangerous for the person's back.

To detect the difference between low and high-intensity movements and further classify them BIRCH clustering algorithm is used (see https://en.wikipedia.org/wiki/BIRCH). For this algorithm we prepare input data which represents set of features extracted from each lift. Input data consists of five floating point numbers (to calculate this numbers we only using part of the lift when the person is rising (bending) up (angle value increasing over time):

1. Angle after lift—relative angle of the device after lift was performed.
2. Area under curve—space under curve of angle, which represents how steep or sloping was the change of lift angle.
3. Cumulative sum of each point of graph.
4. Graph smoothness—coefficient of how smooth the angle changes.
5. Average angular speed—represents how fast person was rising up.

Before a classification can be started samples of lifts are collected. These are split into two groups, one for low intensity lifts and another one for high intensity lifts. Usually at least 100 samples of the lifts is enough to begin classifying.

Each of the five features is different for low-intensity and high-intensity lift but their absolute values are different for each different person. Unsupervised learning is used instead of supervised learning, which may need millions of samples for different categories of people to have a good accuracy. By using unsupervised learning, we have an ability to have a unique intensity detection model for each person which will take in account all the personal differences.

Using five features we have a 5-dimensional space where each dimension is feature value. This 5-dimensional space can be split by zones where the maximum concentration of lift movements occurred. These zones then can be categorized into two categories, one for low-intensity movements and another one for high-intensity.

Figure 14:
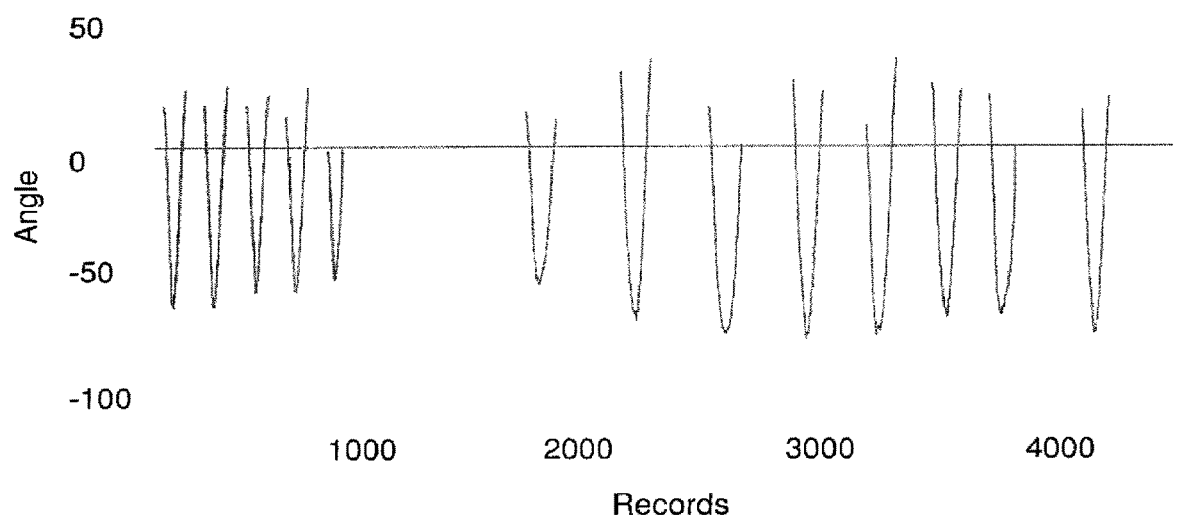
FIG. 14 is a graph of bending angles over time, with a first set (left) being of low intensity and a second set (right) be of high intensity.
Figure 15:
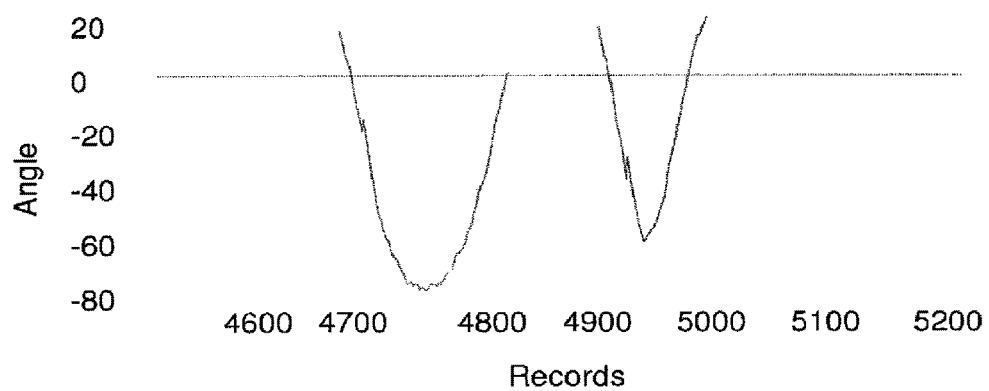
FIG. 15 a graph of other bending angles over time, with a first one (left) being of high intensity and a second one (right) be of low intensity

On graphs in FIGS. 14 and 15, we can see the visual difference between low-intensity and high-intensity movements: low-intensity are quicker, rising curve is more steep, smaller difference in start and stop angle after lift. In both the low intensity lifts are to the left and the high intensity lifts are to the right.

Abstract features may also be used in some embodiments to assess the risk of a movement or series of movements, such as:

max(v), min(v), mean(v), median(v), where v is substituted by each component of accelerometer data (aX, aY, aZ) and accelerometer magnitude, where accelerometer magnitude=$\sqrt{aX^2+aY^2+aZ^2}-1$; and The first twenty coefficients of a Fast Fourier Transformation (FFT) of accelerometer magnitude. In the case where the FFT provides less than 20 coefficients, the missing coefficients are filled in as zero.

The resulting feature list is:
1. Time of the body bending down
2. Time of the body rising up
3. Time of the body in near static posture
4. max(v), where v is bending angle
5. min(v), where v is bending angle
6. mean(v), where v is bending angle
7. median(v), where v is bending angle
8. max(v), where v is twisting angle
9. min(v), where v is twisting angle
10. mean(v), where v is twisting angle
11. median(v), where v is twisting angle
12. max(v), where v is aX
13. min(v), where v is aX
14. mean(v), where v is aX
15. median(v), where v is aX
16. max(v), where v is aY
17. min(v), where v is aY
18. mean(v), where v is aY
19. median(v), where v is aY
20. max(v), where v is aZ
21. min(v), where v is aZ 22. mean(v), where v is aZ
23. median(v), where v is aZ
24. max(v), where v is accelerometer magnitude
25. min(v), where v is accelerometer magnitude
26. mean(v), where v is accelerometer magnitude
27. median(v), where v is accelerometer magnitude
28.-48. 20 coefficients of FFT over accelerometer magnitude.

A model for predicting the relative object weight is determined from the signal features, as input data, and the resulting features, as output data intended to be produced by the model. In an embodiment the model is a decision tree. A regression model is used to determine the characteristics of the decision tree from the input data and the output data. In an embodiment the regression model uses a gradient boosting machine to realize the decision tree. The model may be refined over time.

The relative object weight determined form the input data by the model is then converted into a weight class. The weight class is in turn is used to determine $K_{FO}$.

A training data set with target values of relative weight (mass of an object divided by human mass) of an object which have been picked up or placed to the ground is used by the regression model to determine/refine the characteristics of the model.

To make uniform distribution targets the next sequence of transformation is performed:

$y \rightarrow (\sqrt{y}*100)$ divided without remainder by 17,
where $y$ is a target array.

In order to determine the weight class, the relative object mass $M_r$ is determined as follows:

$$Mr = \frac{Mo}{Mh}$$

where $M_h$ is human mass, and $O_m$ is object mass.

In an embodiment a table of relative object mass to human weight is given in Table 7.

TABLE 10

Relative object mass based on Human mass and Object mass

| Human mass, kg | Relative object mass $M_r$ | | | | | | | | |
|---|---|---|---|---|---|---|---|---|---|
| 40 | 0.00 | 0.13 | 0.25 | 0.38 | 0.50 | 0.63 | 0.75 | 0.88 | 1.00 |
| 50 | 0.00 | 0.10 | 0.20 | 0.30 | 0.40 | 0.50 | 0.60 | 0.70 | 0.80 |
| 60 | 0.00 | 0.08 | 0.17 | 0.25 | 0.33 | 0.42 | 0.50 | 0.58 | 0.67 |
| 70 | 0.00 | 0.07 | 0.14 | 0.21 | 0.29 | 0.36 | 0.43 | 0.50 | 0.57 |
| 80 | 0.00 | 0.06 | 0.13 | 0.19 | 0.25 | 0.31 | 0.38 | 0.44 | 0.50 |
| 90 | 0.00 | 0.06 | 0.11 | 0.17 | 0.22 | 0.28 | 0.33 | 0.39 | 0.44 |
| 100 | 0.00 | 0.05 | 0.10 | 0.15 | 0.20 | 0.25 | 0.30 | 0.35 | 0.40 |
| 110 | 0.00 | 0.05 | 0.09 | 0.14 | 0.18 | 0.23 | 0.27 | 0.32 | 0.36 |
| 120 | 0.00 | 0.04 | 0.08 | 0.13 | 0.17 | 0.21 | 0.25 | 0.29 | 0.33 |
| 130 | 0.00 | 0.04 | 0.08 | 0.12 | 0.15 | 0.19 | 0.23 | 0.27 | 0.31 |
| Object mass $M_o$, kg | 0 | 5 | 10 | 15 | 20 | 25 | 30 | 35 | 40 |

The classes can be allocated to the relative mass as follows:

$$\text{Class \#} = \left(100*\sqrt{\frac{Mo}{Mh}} - \text{mod}\left(\left\lfloor 100*\sqrt{\frac{Mo}{Mh}}\right\rfloor, 17\right)\right)/17$$

This provides a table (Table 11) of normalized classes that can be predicted:

TABLE 11

Relative mass class based on Human mass and Object mass

| Human mass, kg | Class | | | | | | | | |
|---|---|---|---|---|---|---|---|---|---|
| 40 | 1 | 3 | 3 | 4 | 5 | 5 | 6 | 6 | 6 |
| 50 | 1 | 2 | 3 | 4 | 4 | 5 | 5 | 5 | 6 |
| 60 | 1 | 2 | 3 | 3 | 4 | 4 | 5 | 5 | 5 |
| 70 | 1 | 2 | 3 | 3 | 4 | 4 | 4 | 5 | 5 |
| 80 | 1 | 2 | 3 | 3 | 3 | 4 | 4 | 4 | 5 |
| 90 | 1 | 2 | 2 | 3 | 3 | 4 | 4 | 4 | 4 |
| 100 | 1 | 2 | 2 | 3 | 3 | 3 | 4 | 4 | 4 |
| 110 | 1 | 2 | 2 | 3 | 3 | 3 | 4 | 4 | 4 |
| 120 | 1 | 2 | 2 | 3 | 3 | 3 | 3 | 4 | 4 |
| 130 | 1 | 2 | 2 | 2 | 3 | 3 | 3 | 4 | 4 |
| Object mass $M_o$, kg | 0 | 5 | 10 | 15 | 20 | 25 | 30 | 35 | 40 |

Figure 16:
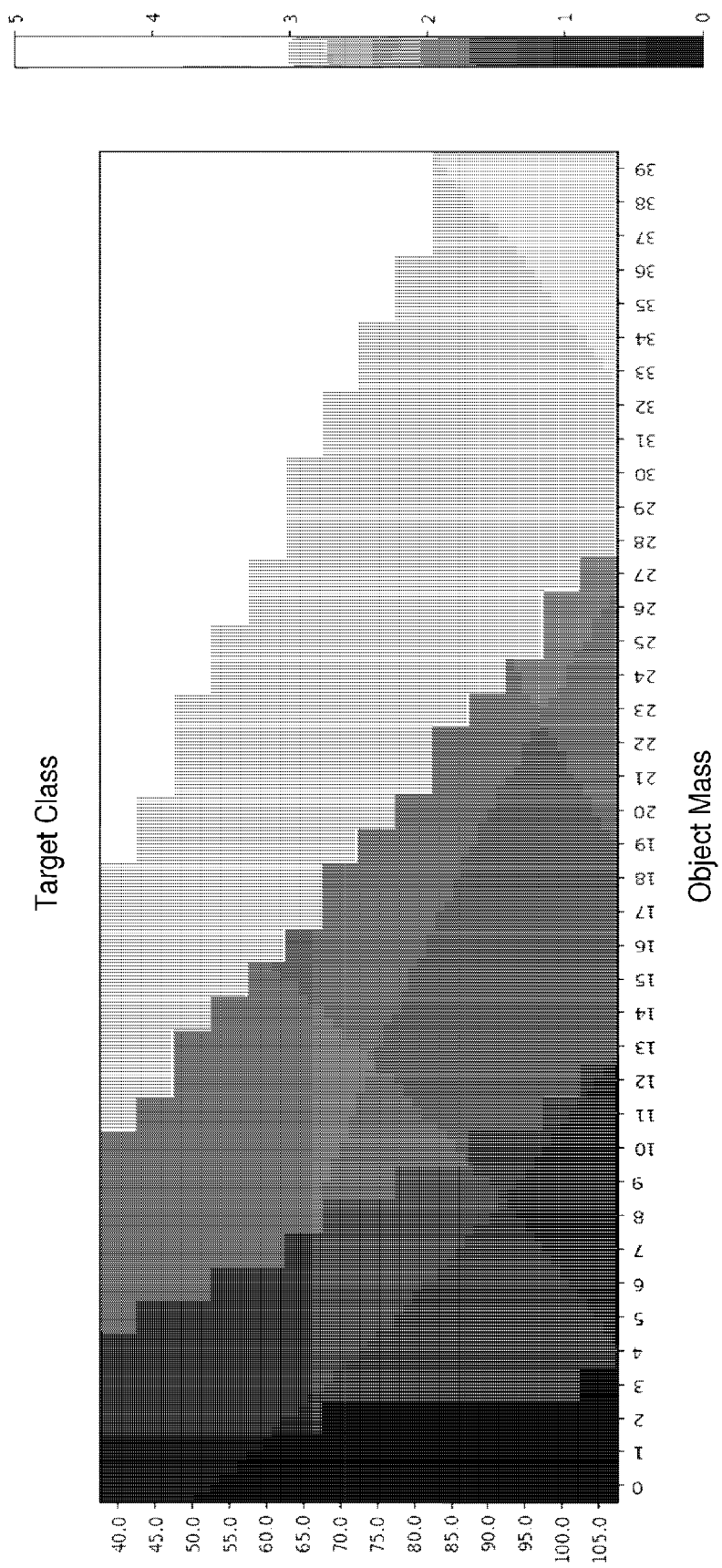
FIG. 16 is a heatmap of a distribution of target classes.

FIG. 16 shows a distribution of target classes on a heatmap.

Figure 17:
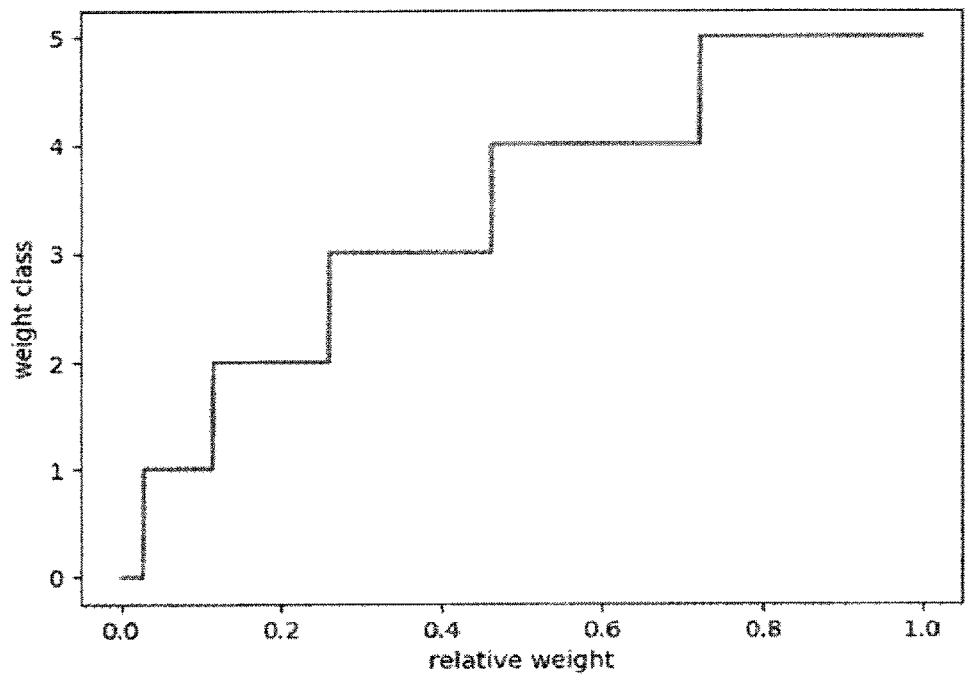
FIG. 17 is a graph of dependencies of weight class against initial relative weight.

FIG. 17 shows dependencies of weight class with respect to initial relative weight.

In an alternative embodiment instead of the two intensity classes noted above, the present invention only uses classes #1, #2, #3, which may be correlated to the 'Light', 'Medium' and 'Heavy' classes. Other correlations are possible.

Constants were defined with respect to the training set. The algorithm is validated and optimized by using cross-validation techniques.

FIGS. 9 to 12 provide graphical representations of example risk scores produced using the method and system of the present invention.

Figure 9:
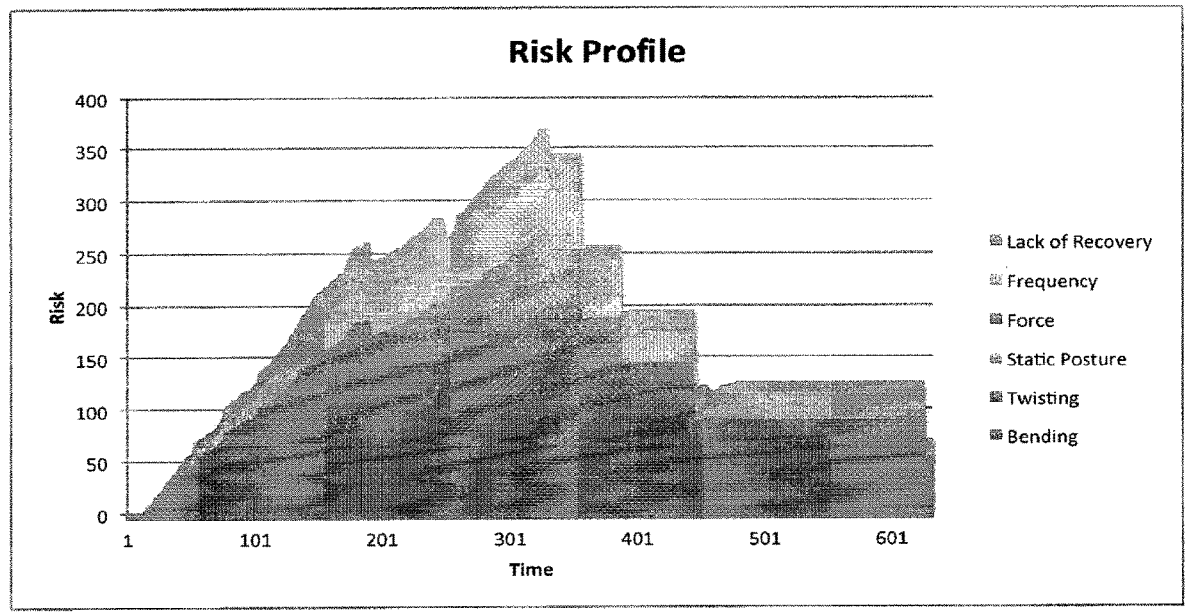
FIG. 9 is an example of a graphical representation of risk scores produced using the method of FIG. 8.

FIG. 9 shows a graph of a risk profile produced by manual labour over time. The risk score is on the y-axis and time is on the x-axis. The risk score is a composite of bending, twisting, static posture, force (exertion), frequency of exertion and lack of recovery. It can be seen that up until about time unit 330 insufficient breaks were taken. However as successive breaks are taken there are significant decreases in risk. The majority of the risk is in bending actions.

Figure 10:
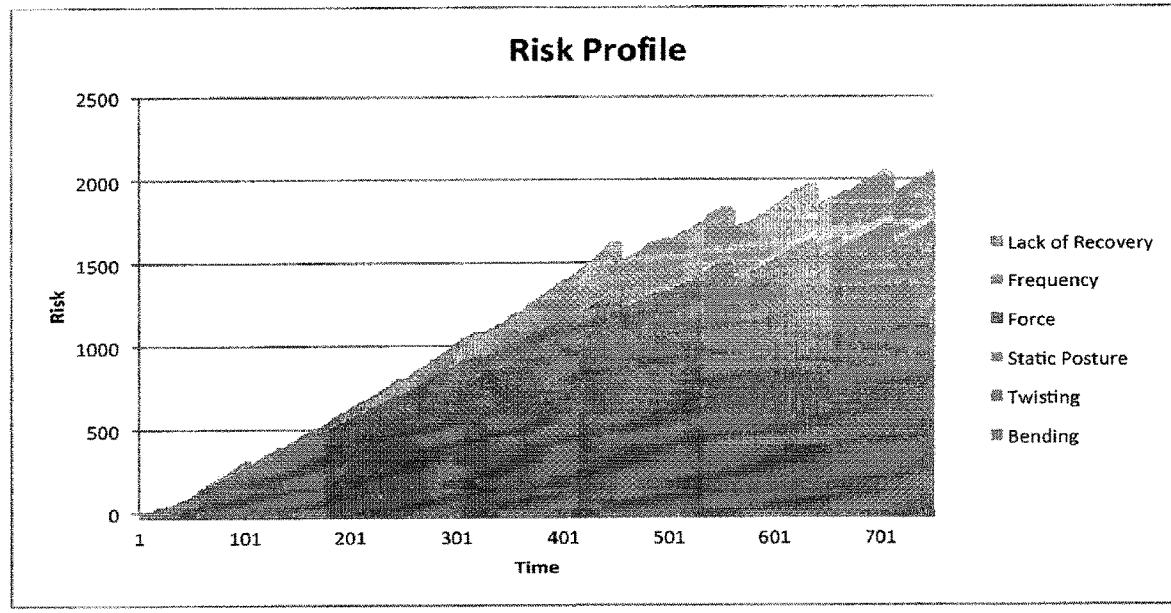
FIG. 10 is another example of a graphical representation of risk scores produced using the method of FIG. 8.

FIG. 10 shows a graph of a risk profile produced by manual labour over time, with the axes and composition of the risk score being the same as those of FIG. 9. It can be seen that up until about time unit 450 no substantial breaks were taken. However the valleys after this time point show that the breaks were insufficient to significantly reduce risk.

Figure 11:
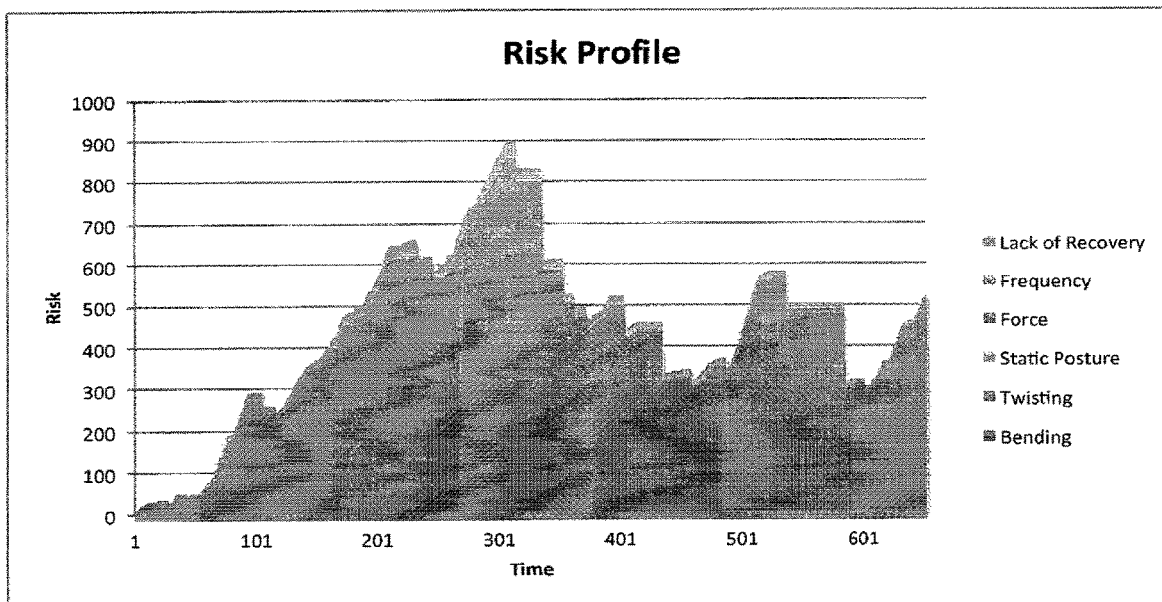
FIG. 11 is another example of a graphical representation of risk scores produced using the method of FIG. 8.

FIG. 11 shows a graph of a risk profile produced by manual labour over time, with the axes and composition of the risk score being the same as those of FIG. 9. It can be seen that there is a peak of risk at about time unit 300, but as corrective action is taken thereafter, such as by providing a warning, the risk can be significantly reduced.

Figure 12:
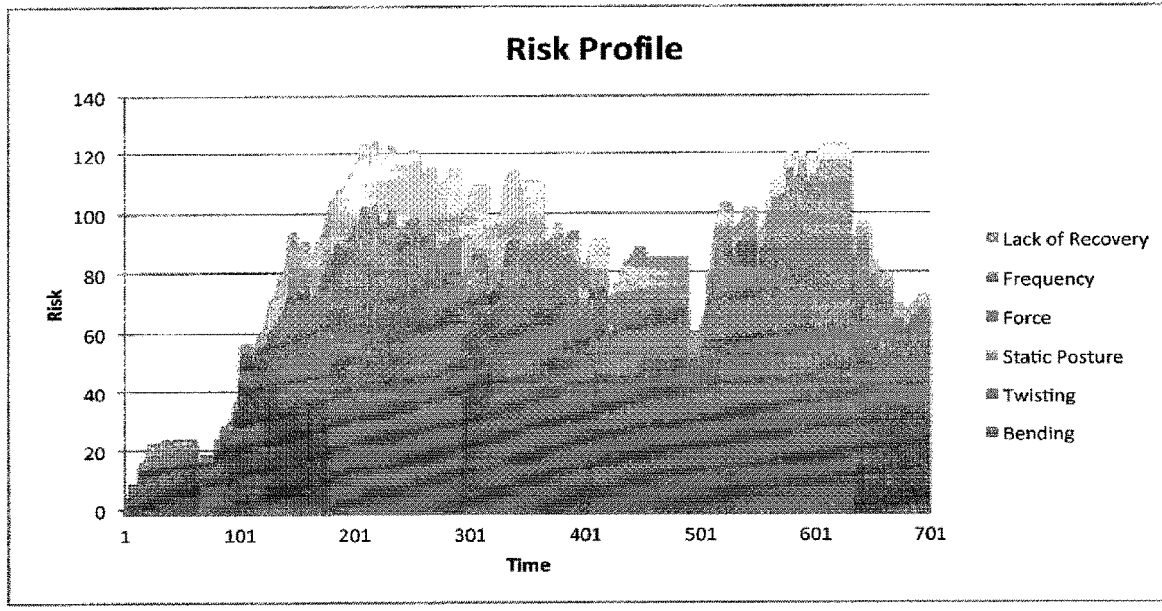
FIG. 12 is another example of a graphical representation of risk scores produced using the method of FIG. 8.

FIG. 12 shows a graph of a risk profile produced by manual labour over time, with the axes and composition of the risk score being the same as those of FIG. 9. It can be seen that the amount of bending risk significantly increased at about time unit 100, with peak risks at about time units 200 and 600, but with the compositions of the risk at these times being different.

In an embodiment the amount of force used during exertion is determined by measuring the duration at which there is bending. In particular the rate of change is measured. The rate of change may be a first order derivative (speed), second order derivative (acceleration) or third order derivative (jerk) measurement. The theory behind this is that when straining, that is applying a lot of force to an object, movement is minimal or slow until momentum in the change of position (angle) is achieved. For example, a change in acceleration can be used to infer the amount of force exerted and thus the weight or load being moved in an action.

The reports provide the advantage of informing the safety officer or other official and the worker of the level of workplace safety and the adoption of risk control mechanisms. The report may also include recommendations based upon the aggregated information.

The report and/or thresholds may be adjusted to each individual user, by factoring in user specific parameters, such as exposure to vibration, side bending, force (Distance between the load and the body, weight of the load, speed of bending and coming up), fatigue, age, weight, height, BMI, and medical history.

In an alternative each movement is determined to be low or high risk or a series of movements have be determined to comprise a number of high risk movement in a period of time, for example per hour or per work period (shift). This high risk movement or the number of high risk movements over time can be communicated to the person working and/or in a safety report in a workforce.

Recommended remedial action can be determined based on the determined risk factors. For example, the following recommendation could be made to mitigate against the determined risk factors:
1. Rotation component can be eliminated or reduced. This will reduce the total risk of low back pain;
2. Reduce duration of being in static posture;
3. Reduction of the angle of bending;
4. Take a 30 second rest break in the middle of the flexion;
5. Reduction of the frequency of lifting.

Reporting on movement risks over an extended period of time, rather than or in addition to on individual movements can create postural awareness of the workers. Reporting might be used to suggest kinesiotaping or biomechanic education of the workers.

Modifications may be made to the present invention within the context of that described and shown in the drawings. Such modifications are intended to form part of the invention described in this specification.

What is claimed is:

1. A system for monitoring core body movement, comprising:
   a sensor device for collecting a data set representing a plurality of separate core body movements being made over time;
   a processor for determining a plurality of risk scores from the data set, wherein determining each of the risk scores comprises determining a set of risk factor coefficients based on the body movements from the data set, each risk coefficient representing a different type of risk associated with body movements, and the risk coefficients being multiplied together in the determining of each of the plurality of risk scores; and
   an output device for indicating the risk scores.

2. The system according to claim 1, wherein the sensor device and the processor are in a single monitoring device for each user.

3. The system according to claim 1, wherein the data set representing body movements comprises a back bending angle and a torso twisting angle of each movement and one of the risk coefficients is based on back bending angle and torso twisting angle.

4. The system according to claim 1, wherein the data set representing body movements further comprises a static posture time of each movement and one of the risk coefficients is based on the static posture time, wherein the static posture time is the time at which the posture during the movement is static.

5. The system according to claim 1, wherein one of the risk factor coefficients is based on frequency of activity, wherein the frequency is how often a set of movements occurs.

6. The system according to claim 1, wherein one of the risk factor coefficients is based on a duration of rest between movements.

7. The system according to claim 1, wherein one of the risk factor coefficients is based on a duration of activity before rest.

8. The system according to claim 1, wherein one of the risk factor coefficients is based on an amount of predicted exertion in each movement.

9. The system according to claim 1, wherein one of the risk factor coefficients is based on a frequency of movements in a given time before a rest occurs.

10. The system according to claim 1, wherein one of the risk factor coefficients is based on a value determined by the amount of classified exertion in each movement as a function of angle measurements over time.

11. The system according to claim 1, wherein the risk factor coefficients comprise a value determined by one or more of the following: the amount of time taken to bend down; the amount of time to bend up, the jerkiness of a movement, the angle of the torso at the end of the movement, the smoothness of acceleration through the movement, the area under a curve mapping an angle of bending of a movement over time, and the sum of acceleration of a movement over time.

12. The system according to claim 1, wherein the processor for determining the plurality of risk scores is configured to determine the amount of exertion by determining a period of time at which a user is bending and twisting.

13. The system according to claim 1, wherein the determined amount of exertion is used to calculate an inferred weight being handled by a user.

14. The system according to claim 1, wherein the risk factor coefficients are progressively determined over time, by cumulative analysis of the data set over a working period.

* * * * *